(12) United States Patent
Portney (10) Patent No.: US 8,619,362 B2
(45) Date of Patent: Dec. 31, 2013

(54) MULTIFOCAL DIFFRACTIVE OPHTHALMIC LENS WITH MULTIFOCAL BASE SURFACE

(76) Inventor: Valdemar Portney, Newport Coast, CA (US)

( * ) Notice: Subject to any disclaimer, the term of this patent is extended or adjusted under 35 U.S.C. 154(b) by 1056 days.

(21) Appl. No.: 12/625,364

(22) Filed: Nov. 24, 2009

(65) Prior Publication Data

US 2010/0066973 A1    Mar. 18, 2010

(51) Int. Cl.
*G02B 5/18* (2006.01)
(52) U.S. Cl.
USPC ........................ 359/569; 359/574; 351/159.11
(58) Field of Classification Search
None
See application file for complete search history.

(56) References Cited

U.S. PATENT DOCUMENTS

| 4,637,697 | A | * | 1/1987 | Freeman | 351/159.44 |
| 5,056,908 | A | * | 10/1991 | Cohen | 351/159.44 |
| 5,112,351 | A | * | 5/1992 | Christie et al. | 623/6.28 |
| 5,121,980 | A | * | 6/1992 | Cohen | 351/159.41 |
| 2006/0116764 | A1 | * | 6/2006 | Simpson | 623/6.23 |

* cited by examiner

*Primary Examiner* — Arnel C Lavarias
(74) *Attorney, Agent, or Firm* — Hackler Daghighian & Martino (57) ABSTRACT

A multifocal ophthalmic lens includes a lens element having an anterior surface and a posterior surface, a refractive zone, or base surface having produced multifocal powers disposed on one of the anterior and posterior surfaces; and a near focus diffractive multifocal zone disposed on one of the anterior and posterior surfaces.

6 Claims, 7 Drawing Sheets

MULTIFOCAL DIFFRACTIVE OPHTHALMIC LENS WITH MULTIFOCAL BASE SURFACE

FIELD OF THE INVENTION

The present invention relates generally to multifocal ophthalmic lenses, and more particularly to multifocal lenses which provide diffractive powers for distance, intermediate and near vision.

BACKGROUND OF THE INVENTION

Ophthalmic lens is defined as a lens suitable for carrying on the eye or inside the eye. Also included are less common vision correction lenses such as artificial corneal and lamellar corneal implants.

A fixed single power lens provides good quality of vision but only within a small range of viewing distances that is usually significantly narrower than the range required from near to distant vision. There is a significant effort to develop a lens for presbyopia correction in a form of refractive or diffractive type lenses. This type of the implant provides a number of powers, so called bifocal or multifocal lens. Reference to bifocal or multifocal terminology is used herein interchangeably. The multifocal ophthalmic lens can provide refractive powers, diffractive powers or a combination of both. A multifocal diffractive lens includes multifocal diffractive surface to provide near focus and opposite refractive surface. The "opposite surface" means the refractive surface of the diffractive lens which is opposite to the surface with a diffractive zone with light passing through both the region of the opposite refractive surface and diffractive zone.

A diffractive lens generally consists of a number of annular surface zones of equal area, so called Fresnel type zones or grooves. The optical steps are provided between the adjacent zones that follow the specific rule hereinbelow described. If step sizes are zero or randomly sized or groove areas are randomly sized, the lens becomes a refractive type, i.e. the corresponding image locations are defined by Snell's law.

Figure 1:
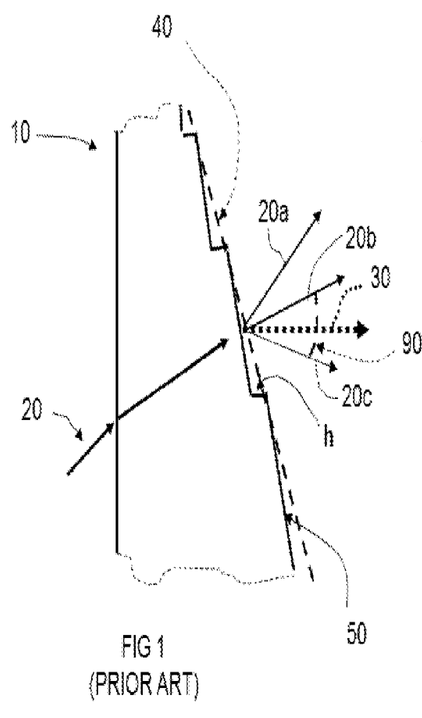
FIG. 1 illustrates a prior art diffractive lens with blazed periodic structure forming different diffraction orders along which the light can only be channeled. The FIG. 1 also include a description of a "geometrical model" of the diffractive lens through the relationship between the blaze ray defined by the refraction at the blaze and directions of the diffraction orders.

A diffractive lens can be considered as a combination of refractive surface formed by zero step size so called base curve or base surface and phase grating, see FIG. 1. Per the prior art, base surface is being spherical surface or aspheric surface that corrects for spherical aberration of the spherical refractive lens of the equivalent power. Equivalent power lens in general means that that original lens and the it is compared to as the lens of the equivalent power both have the same power surfaces as well. In this respect one can reference to equivalent power surface also.

A spherical refractive lens forms a quasi-spherical wavefront deviated from a perfect sphere due to a spherical aberration. The aspheric lens that corrects for spherical aberration creates a spherical wavefront. The amount of aberration produced by a spherical ophthalmic lens is usually small enough for pupils up to about 4 mm to assume the spherical shape of the corresponding wavefront. As a result, both spherical lens and aspheric refractive lens with spherical aberration correction are treated the same for phase grating calculation in the diffractive optic. From this stand point both types of diffractive lenses with spherical base surface and aspheric base surface with spherical aberration correction, are equivalent for phase (diffraction) grating calculation and, therefore, will be referenced in this disclosure as "spherical lens" or "spherical surface" to avoid a multiple repetition of the reference to "aspheric with correction for spherical aberration".

A phase grating can be formed by different types of zone or groove shapes with a blaze shape shown on the FIG. 1 being the most common one. A specific periodic blaze shape is cut into a spherical refractive surface which becomes the base surface of the diffractive surface or diffractive lens. The resulted blaze shapes create a phase grating, i.e. a periodic array of optical scattering regions. This disclosure will use blaze grating as an example but the present invention is applied to any type of phase grating that produces distance and near foci.

A periodic structure of the phase grating is such that it creates constructive interference of light at different angles depending on wavelength of light which are called diffraction orders. The corresponding wavelength of light used to design the phase grating is called design wavelength. The directions of the diffraction orders and corresponding image locations are defined by the Grating formula, not Snell's law. The key point for the phase grating to form distinct diffraction orders, is to have equal areas of the grooves and equal Optical Path Differences (OPD) between adjacent grooves at their borders in the direction of each diffraction order.

The distances from the grating to the foci created by the diffraction orders can be quantified in terms of diffraction powers associated with the diffraction orders similarly to a refractive lens power definition. Zero-order diffractive power of the diffractive lens coincides with the refractive power of the refractive lens formed by the base surface of the diffractive lens and its opposite refractive surface and, as a result, loosely called refractive power of the diffractive lens.

According to the wave nature of light, constructive interference of light occurs if electromagnetic wave of light is in phase at the corresponding image location. The constructive interference is maintained if the light from the grooves is shifted by the full phase equaled to integer number of the design wavelength. For instance, zero order corresponds to the original direction of the light produced by the refractive lens formed by the base surface and opposite surface of the diffractive lens, i.e. zero phase shift between light coming from each adjacent blaze zone; $1^{st}$ order is produced by the phase of one wavelength shift between each adjacent blaze; $2^{nd}$ order is produced by the phase of two wavelengths shift between each adjacent blaze and so on. Thus, grating period or groove width determines an angle of the given diffractive order from the zero-order direction, i.e. the location of a higher order focus from the zero-order focus and, therefore, the responsible for the corresponding diffractive powers of high diffraction orders.

By the law of formation of a diffraction order, light can only be channeled along the diffraction orders of the diffractive lens where constructive interference can take place. It leads to the discrete foci of a diffractive lens. In addition, the image is physically formed at a given foci if a measurable percent of total light is actually channeled along a given diffraction order. This depends upon the light phase shift introduced by each blaze zone, i.e. blaze material thickness (h), FIG. 1. The percent of total light at a given order is called diffraction efficiency of this order. In general, one can call it also a light transmittance for the given order.

According to the "geometrical model" of the grating, 100% efficiency (light transmittance) in m-order can be achieved if the direction of the blaze ray defined by the refraction at the blaze coincides with the direction of m-order diffraction, (Carmiña Londoño and Peter P. Clack, Modeling diffraction efficiency effects when designing hybrid diffractive lens systems, Appl. Opt. 31, 2248-2252 (1992)). It simply means that the blaze material thickness is designed to direct the blaze ray along the m-order diffraction produced by the blaze groove widths for the design wavelength of light.

The "geometrical model" provides a simple explanation of the diffractive lens structure which is important in explaining the present invention instead of introducing the mathematics of phase function, transmission function and its Fourier series to calculate diffraction efficiencies and solving the diffraction integral for light intensity distribution between the diffraction orders.

For instance, if the blaze ray is refracted along the middle direction between zero-order and (−1)-order, then the diffraction efficiency is equally split between zero-order and (−1)-order. The corresponding blaze height is half of the one required for 100% efficiency for (−1)-order to allow the groove surface to refract the blaze ray in the middle direction. Still one has to go through a formal process of calculation to determine that the diffraction efficiencies of (−1)-order and zero-order each equals to 40.5% at the design wavelength with the rest of light is spread out between other orders of diffraction. The described above diffraction lens is a typical configuration of a bifocal (multifocal) diffractive lens used for contact lens and intra-ocular lens platforms.

In a simple paraxial form the circular grating zones, also called grooves, echelettes or surface-relief profile, can be expressed by the formula $r_j^2 = jm\lambda f$, i.e. the focal length of m-order diffraction (m=±1, ±2, etc) for the design wavelength ($\lambda$) can be closely approximated by the following formula:

$$f_m = \frac{r_j^2}{jm\lambda}$$

This is the formula used in the prior art of the groove widths calculation in multifocal diffractive optic with spherical base surface or aspheric base surface that corrects for spherical aberration of the equivalent power spherical lens, The location of groove's borders are simply determined by $r_j$. The formula (1) is based upon the condition that the wavefront produced by the equivalent power refractive lens formed by the base surface of the diffractive lens and its opposite refractive surface is a spherical wavefront that focuses into a single point-focus at each diffraction order.

In the paraxial approximation the blaze material thickness to produce 100% efficiency at m-order is $$h_m = \frac{m\lambda}{(n - n')} \quad (2)$$

where n=refractive index of the lens material and n'=refractive index of the surrounding medium. Half of the blaze thickness in the formula (2) is used to produce bifocal diffractive lens with 40.5% of light directed to zero-order allocated to far focus and (−1)-order allocated to near focus, i.e. m=1.

A diffractive surface may be formed by different shapes of the periodic diffractive structure and not only by a blaze shape and for the generality of the present invention the term "groove" is used as the description of the variety of shapes of the diffractive structure including multiorder phase grating.

U.S. Pat. No. 5,096,285 by Silberman describes diffraction surface with 100% efficiency to provide single diffraction power and the invention does not utilize the main advantage of the diffractive optic to use several diffraction orders (zero and −1, or +1 and −1, etc.) to reduce pupil dependency of the bifocal ophthalmic lens performance.

U.S. Appl. No. 20050057720 by Morris describes also diffractive 100% efficiency surface with the utilization of multiorder diffractive surface (MOD), i.e. the zones having boundary condition of phase shift by the multiple wavelength to provide similar diffraction efficiency for the range of wavelengths instead of only for the design wavelength.

Cohen and Freeman are the principal inventors of ophthalmic multifocal diffractive optic that utilizes several diffractive orders to form image from the objects at different distances. The Cohen patents: U.S. Pat. Nos. 4,210,391; 4,338,005; 4,340,283; 4,881,805; 4,995,714; 4,995,715; 5,054,905; 5,056,908; 5,117,306; 5,120,120; 5,121,979; 5,121,980 and 5,144,483. The Freeman patents: U.S. Pat. Nos. 4,637,697; 4,641,934; 4,642,112; 4,655,565, 5,296,881 and 5,748,28 where the U.S. Pat. No. 4,637,697 references to the blaze as well as step-shapes (binary) diffractive surface.

Other patents on diffractive lenses have been granted to Futhey: U.S. Pat. Nos. 4,830,481, 4,936,666, 5,129,718 and 5,229,797; Taboury: U.S. Pat. No. 5,104,212; Isaacson: U.S. Pat. No. 5,152,788; Simpson: U.S. Pat. Nos. 5,076,684 and 5,116,111 and Fiola: U.S. Pat. Nos. 6,120,148 and 6,536,899.

Swanson in U.S. Pat. No. 5,344,447 describes tri-focal lens using binary type diffractive surface profile. Kosoburd in U.S. Pat. No. 5,760,871 also describes tri-focal lens with blaze and binary profiles.

Several patents describe the variable step size between the adjacent zones of the diffractive structure to control light transmittance at different diffraction orders with pupil size: U.S. Pat. Nos. 4,881,805 and 5,054,905 by Cohen describe so called progressive intensity bifocal lens where the step size at the adjacent zones reduced towards periphery to shift larger portion of light towards zero-order (far focus) diffraction image, i.e. to control light transmittance to the given order with pupil diameter. Baude et al in U.S. Pat. No. 5,114,220 discloses an ophthalmic lens which characteristically comprises at least two concentric regions having diffractive components with different phase profiles in order to use different orders of diffraction. Lee et al in U.S. Pat. No. 5,699,142 incorporates a similar concept into so called apodized lens by recommending the specific reduction in echelettes heights, so called apodization the diffractive surface echelettes heights, to split light initially equally between Far and Near foci (40.5% efficiency for each) and then the heights reduce towards lens periphery to shift larger portion of light towards far focus with larger pupil size, i.e. to control light transmittance with pupil diameter. Freeman in U.S. Pat. No. 5,748, 282 also refers to the variable step size to control light intensity between different orders with pupil size variation.

U.S. Pat. No. 5,056,908 discloses an ophthalmic contact lens with a phase plate and a pure refractive portion within its optic zone that is placed at the periphery of phase zone area. U.S. Pat. No. 5,089,023 by Swanson also describes the lens with a combination of single focus refractive and diffractive segments that can be of bifocal design. In both inventions the refractive portion coincides with one of the diffractive order either for distant or near vision.

Tecnis multifocal diffractive lens (Tecnis MIOL) by Abbott Medical Optics includes refractive aspheric surface as the opposite surface to the diffractive surface. This aspheric surface is the front surface of the lens and multifocal diffractive structure is placed on the back of the lens. The lens formed by aspheric opposite and spherical base surfaces create distant focus (zero-order) and the diffractive structure produces near focus as (−1) order diffraction. The aspheric surface is to correct for spherical aberration of the equivalent power spherical lens and is to improve image contract at distant vision for large pupils above 4 mm diameter as compared with equivalent power bifocal diffractive lens with opposite spherical refractive surface.

U.S. Pat. Appl. No. 2006/0116764 by Simpson describes an aspheric multifocal diffractive lens with the base surface serving as an aspheric surface of the multifocal diffractive surface. The opposite refractive surface is spherical surface and together with aspheric base surface forms aspheric lens that is technically equivalent to Tecnis aspheric lens formed by aspheric opposite and spherical base surfaces as the aspheric base surface is also to correct for spherical aberration of the equivalent power bifocal diffractive lens with spherical base surface in order to improve image contrast of distant image at large pupils as compared with a multifocal diffractive lens with spherical base surface of equivalent power.

There is a downside in aspherization per Tecnis MIOL and Simpson's designs as it increases sensitivity to refractive error due to reduced Depth of Focus at far focus. A reduction in aberrations improves the vision quality (image contrast) as compared with spherical lens of equivalent power but reduces a depth of focus meaning more rapid image quality degradation with a small deviation from the best focus position. Best focus position is defined as the position where the image quality is the best as defined by a selected quality metric. For instance, smallest spot size, maximum contrast, maximum Modulation transfer function or maximum Strehl ratio.

It has been shown that bifocal diffractive lens demonstrates two distinct intensities at two foci for distant and near vision (Golub M A, et al, Computer generated diffractive multifocal lens. J. Modern Opt., 39, 1245-1251 (1992), Simpson M J. Diffractive multifocal intraocular lens image quality. Appl. Optics, 31, 3621-3626 (1992) and Fiala W and Pingitzer J. Analytical approach to diffractive multifocal lenses. Eur. Phys. J. AP 9, 227-234 (2000)). Diffractive optic offers the advantage to provide these foci independently to pupil diameter. Nevertheless, common to all diffractive designs of is the fact that a bifocal diffractive lens is lacking intermediate vision because there is no provision for intermediate focus.

All prior art multifocal diffractive lenses including Tecnis multifocal and the design described by Simpson in U.S. Pat. Appl. No. 2006/0116764 are lacking important attributes to further advance multifocal ophthalmic optic:

(a) intermediate focus (viewing of a computer screen, for instance) and
(b) low sensitivity to refraction error as the lens performance should not depredate significantly with inherent errors of IOL power calculation.

In U.S. Pat. No. 7,073,906 by Portney intermediate focus was introduced to multifocal diffractive lens through refractive power by placing a refractive zone of multifocal power internally to a diffractive bifocal zone which produced only distant and near foci. The present invention expends the intermediate power region to the diffractive power. The regions is also to increase Depth of Focus at distance focus as compared with equivalent power diffractive lens with spherical opposite and base surfaces.

The objective of the present invention is to provide a multifocal diffractive lens that offers a vision range from far through intermediate to near. The related objective of the present invention is to provide multifocal diffractive lens with extended depth of focus (DOF) at far image in order to increase tolerance of distant vision to refraction error.

SUMMARY OF THE INVENTION

A lens in accordance with the present invention consists of front and back surfaces. The lens includes multifocal diffractive grooves to create a multifocal diffraction optic for near and distant foci and multifocal surface on the other surface of the lens, so called "opposite surface" that includes intermediate foci in addition to distant foci or range of foci that includes distant focus. Another embodiment of this invention includes multifocal diffractive zone that produces near focus and is formed on the multifocal base surface of the diffractive structure to yield intermediate focus in addition to distant focus or a range of foci that includes distant focus. Thus, the multifocal diffractive lens of the present invention includes a multifocal opposite surface or multifocal base surface generating a range of foci that includes distant focus to increase depth of focus at distant vision as compared with equivalent power diffractive lens made of spherical opposite surface and spherical base surface. The multifocal diffractive lens of the present invention includes a multifocal opposite surface or multifocal base surface generating intermediate focus in addition to far focus in order to provide a range of powers or several discrete powers.

A form of the multifocal opposite surface or multifocal base surface can be a non-spherical continuous surface to provide a range of powers that includes the distant power. The form of the multifocal opposite surface or multifocal base surface may also be a surface with discrete set of powers that enhances depth of focus (DOF) around distant vision or introduce intermediate focus in addition to distant focus. All above surface forms produce varying combinations of powers that lie below near power level as the discrete near power is produced by the diffractive structure of the multifocal diffractive lenses of the present invention.

In regard to a near focus produced by the phase grating of the diffractive surface, there is advantage to focusing into a single near focal point, i.e. to produce near focus of constant diffractive power. The reason is that a subject commonly controls a distance to a near object and be able adjust for best focus position. Therefore, there is a benefit to reduce aberration at near focus by maximizing near image contrast because a depth of focus, i.e. image sensitivity to a deviation from near best focus, is not an issue in near vision.

The multifocal refractive opposite surface or multifocal base surface may cover only a portion of the corresponding refractive surface or diffractive surface but the definition of the "opposite surface" or "base surface" used in the present invention includes full image forming area of the lens surface. For instance, a multifocal refractive zone may occupy a central portion of the lens and diffractive zone is an annulus around it but the term "base surface" used in the present invention covers the full image forming area of the diffractive surface including the refractive region. The light passes through both the opposite surface and diffractive surface of the multifocal lens per the present invention regardless where the diffractive zone is located within the lens surface.

The described above two embodiments of multifocal opposite surface or multifocal base surface are structurally different but they provide the same optical outcome because their multifocal effect produced by the opposite surface or base surface is optically equivalent. The diffractive structure that produces multiple diffraction orders including near image interfaces with a wavefront created by both surfaces (opposite and base surfaces) regardless which one incorporates a multifocal shape in accordance with the present invention. Both surfaces, opposite and base surfaces may be made multifocal surfaces but this would increase a cost of making the lens and functionally it is not necessary.

An inclusion of a multifocal shape into the base curve or opposite refractive surface of a prior art such spherical base surface or aspheric surface that corrects for spherical aberration as described by Simpson's design or Tecnis multifocal design results in a defective diffractive lens due to near image quality reduction. Near image of a diffractive multifocal optic is created by a constructive interference at the corresponding diffraction order, usually (−1)-order. The inclusion of multifocal surface that involves intermediate or range of foci around distant creates a non-spherical wavefront of a complex non-spherical shape which significantly deviates from the spherical wavefront required for the phase grating (groove widths) calculation per the formula (1). As a result, a constructive interference of the light in the corresponding phase grating can't take place at the near focus and the near image becomes distorted. The objective of this invention is to introduce the method of calculating the diffraction grooves in the presence of the multifocal base surface or multifocal opposite refractive surface which preserves constructive interference at the near focus and resulting in high quality multifocal optic.

The multifocal base surface may be such that the curvature increases to some intermediate power level and then reduces to distant power level or even beyond the distant focus. The changes between intermediate and far power levels may repeat several times continuously or in discrete steps to minimize an impact of pupil diameter variation. As a result, the zero-order image is spread over intermediate and distant foci. A similar multifocal surface that introduces intermediate focus in addition to distant focus or enhances depth of focus of distant vision can also be placed on the surface opposite to the base surface with light passing though both surfaces in sequence.

The appropriate diffractive structure placed on any of the surfaces of the optical system must take into account contributions of all ocular system surfaces to create the final near focus spherical wavefront at the exit aperture of the eye optical system. A multifocal surface can be a posterior surface of the aphakic IOL that replaces natural crystalline lens, i.e. it is the last surface of the eye optical system, or anterior surface of a contact lens placed on the cornea of the eye, or the first surface of the ocular system, or a surface in between such back surface of the contact lens, a surface of corneal implant or aphakic lens or anterior surface of aphakic lens. There is no limitation on the material used as any approved material applied to the ophthalmic optic can be utilized for the multifocal diffractive lens of the present invention.

BRIEF DESCRIPTION OF THE FIGURES

FIG. 2 illustrates a portion of the multifocal diffractive lens of the present invention with blazed periodic structure forming multifocal base surface for zero-order and (−1)-order diffraction for near focus along which the light are channeled. The diffraction structure is placed on the posterior surface of the lens but it can be placed on the anterior surface as a different embodiment. A multifocal surface of the present invention that includes intermediate in addition to far focus or range of foci around distant focus, can be also placed at the opposite refractive surface as a different embodiment with the same optical outcome of light distribution between the diffraction orders. The FIG. 2 incorporates a description of the "geometrical model" of the diffractive lens through the relationship between the blaze ray defined by the refraction at the blaze and directions of the diffraction orders;

DETAILED DESCRIPTION

FIG. 1 describes a portion of a prior art diffractive lens 10 with blazed periodic structure 50 creating diffraction orders indicating by the directions 20a, 20b, 20c, etc. along which the light can only be channeled. The lens 10 is a bifocal lens with the base surface being spherical surface or aspheric with spherical aberration correction. The FIG. 1 includes input light ray 20 refracted by the lens 10. It also shows the refractive base curve 40 that would refract the exiting ray corresponding to the input ray 20 along the direction of zero-order diffraction 20b. Direction of (+1)-order diffraction is shown by 20a and (−1)-order diffraction by 20c. There are infinite orders of diffraction.

The FIG. 1 incorporates a reference to the "geometrical model" of diffractive lens by including blaze ray 30 as the ray corresponding to the input ray 20 and refracted at the blaze. The direction of the blaze ray 30 differs from the direction of 0-order diffraction 20b due to the different refraction angles of the rays at the base curve 40 and blaze structure 50. A particular blaze angle is created by the selection blaze material thickness (h).

The near focus must be closer to the diffractive lens than distance focus and this is the reason to utilize (−1)-order diffraction demonstrating by ray 20c and whereas zero-order is taken for distance. The angular separation between these orders defines angular add power 90. The corresponding separation between near and distance foci in diopter powers defines add power. The angular separation and add power are constant in multifocal diffractive lenses of the prior art.

If the blaze material thickness h is zero than the blaze structure 50 coincides with the base curve 40 and the lens becomes refractive type. If the blaze material thickness (h) increases to refract the blaze ray 30 along (−1)-order of diffraction 20b the lens becomes a Kinoform with 100% efficiency at (−1)-order diffraction. The blaze material thickness in the FIG. 1 is selected to place the blaze ray 30 at the middle between 0-order and (−1)-order diffraction to equally channel the light between these two orders. The rigorous diffraction theory demonstrates that maximum 40.5% of light can be channeled along each of these two orders for the given design wavelength with the rest of the light is spread out between other diffraction orders. In the present multifocal diffractive designs 0-order diffraction is selected to coincide with the power for Far vision (Far power) and (−1)-order coincides with the power required for Near vision (Near power).

Figure 2:
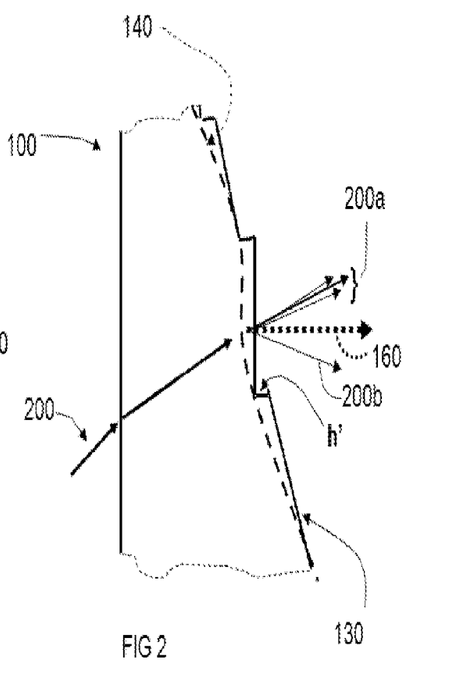

FIG. 2 describes a portion of diffractive lens 100 in accordance with the present invention with blazed periodic structure 130 creating diffraction orders indicating by the directions 200a (zero-order) and 200b (higher order), etc. along which the light can only be channeled. The figure includes input light ray 200 refracted by the lens 100. It also shows the multifocal base surface 140 that would refract the exiting ray corresponding to the input ray 200 along the directions of zero-order diffraction 200a of the given lens region.

The bunch of rays 200a shown on FIG. 2 represents the range of rays that would be produced by the multifocal base surface at different lens surface locations. They coincides with the range of rays at zero-order diffraction in the multifocal diffractive lens of the present invention. Instead of placing each ray at the corresponding location of the multifocal base curve, the rays 200a are combined at one surface location to depict relative differences in the directions of the rays at different locations of the multifocal surface. The range of rays is to include a direction to intermediate focus in addition to far focus or produce a range of foci around the far focus to enhance depth of focus at far focus as compared with the multifocal diffractive lens of equivalent power with spherical base surface. The equivalent power coincides with the power corresponding to the best focus of the multifocal diffractive lens of the present.

Direction of (−1)-order diffraction is shown by 200b as the single ray because of the corresponding single focus position. Single focus design is acceptable for near because the patient can adjust a distance to near object to achieve the best focus without a need for an extended depth of focus.

The multifocal shape functionally analogous to the multifocal base surface may be applied to the opposite refractive surface of the multifocal diffractive lens of the present invention instead of the base surface. The base surface may become a spherical shape or aspheric shape for spherical aberration correction. In either case the multifocal region placed on the base curve of the diffraction zone or the opposite surface, the zero-order diffraction forms a wavefront of a complex non-spherical shape that forms intermediate focus in addition to far or range of foci around far focus to increase depth of focus around far focus as compared with the multifocal diffractive lens of equivalent power with spherical base surface.

The FIG. 2 incorporates a reference to the "geometrical model" of diffractive lens by including blaze ray 160 as the ray corresponding to the input ray 200 and refracted by the groove's blaze. The direction of the blaze ray 160 differs from any of directions of 0-order diffraction 200a due to the different refraction angles of the rays at the base surface 140 and blaze structure 130. The angle difference is created by the blaze material thickness (h').

Figure 3:
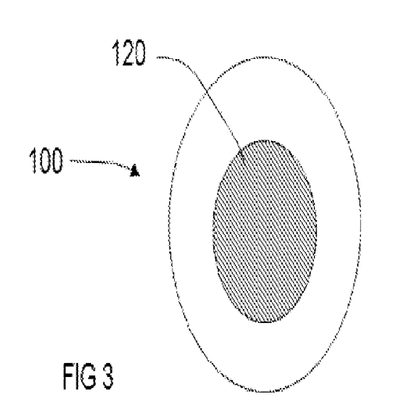
FIG. 3 is a plan view of a preferred embodiment of a lens made in accordance with the present invention, which has multifocal diffractive central zone.

FIG. 3 is a plan view of a preferred embodiment of the ophthalmic lens 100 made in accordance with the present invention which incorporates multifocal diffractive central zone 120. FIG. 3 demonstrates the central zone 120 of a spherical configuration but other suitable configuration may be utilized. For example, a multifocal diffractive zone 120 may be spherical configuration or within a segment or annular with variable radii. The enhancing DOF multifocal region can be introduced to a base surface of the multifocal diffractive zone or on the opposite surface of the multifocal diffractive lens of the present invention but with the light passing through both to form multiple orders of diffraction. As the result, zero-order diffraction in both cases (multifocal base surface or multifocal opposite refractive surface) is of multifocal form that includes intermediate and far foci or may be shaped to enhance depth of focus around distant vision as compared with the multifocal diffractive lens of equivalent power with spherical base surface and opposite spherical refractive surface.

Figure 4:
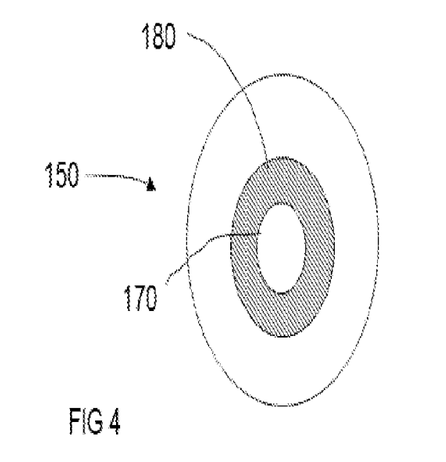
FIG. 4 is a plan view of a preferred embodiment of a lens made in accordance with the present invention, which has multifocal diffractive zone as an annulus.

FIG. 4 is a plan view of another preferred embodiment of an ophthalmic lens 150 made in accordance with the present invention which has multifocal diffractive zone 180 placed outside the central refractive or diffractive zone 170. The enhancing DOF multifocal region can be included into the base surface of the multifocal diffractive zone or on the opposite surface of the multifocal diffractive lens per the present invention but with light passing through both zones to form multiple orders of diffraction by the phase grating. As the result, the zero-order diffraction in both cases (multifocal base surface or multifocal opposite surface) is of multifocal form that includes intermediate and far foci or shaped to enhance depth of focus around distant vision as compared with the multifocal diffractive lens of equivalent power with spherical base surface and opposite spherical refractive surface.

The FIG. 4 demonstrates central zone 170 to be of a spherical configuration but for generality it may be of any configuration located centrally to the multifocal diffractive zone 180.

Figure 5:
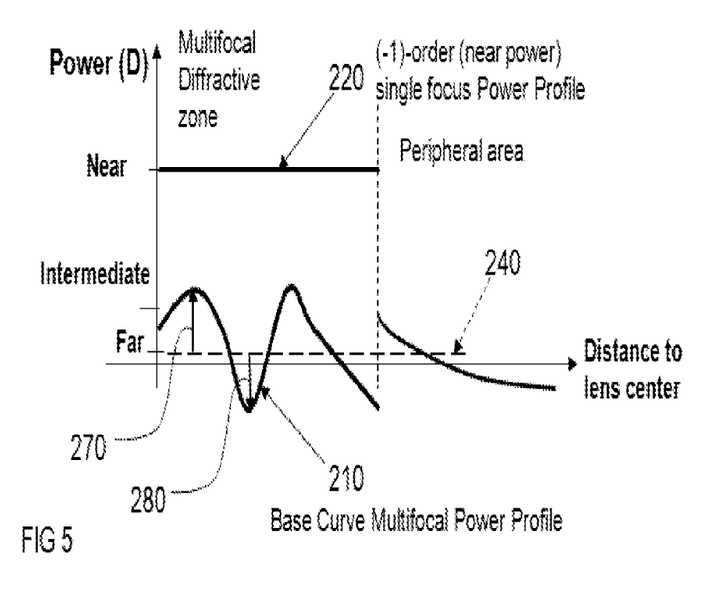
FIG. 5 shows a Power Profile of the lens described in the FIG. 3.

FIG. 5 demonstrates a Power graph of the lens described by the FIG. 3 where the power profile of the base surface includes far and intermediate foci. Thus, the corresponding base surface is called multifocal base surface as it is characterized by a multifocal power profile. This multifocal power profile might be continuously varied as shown on the FIG. 5 or a combination of discrete intermediate and far powers. FIG. 5 shows the multifocal base surface power profile modulate between powers of intermediate and far power ranges in order to reduces sensitivity to eye pupil variation. The power corresponding to the best far focus defines the average power of the multifocal power profile of the multifocal base surface and is shown by the horizontal broken line drawn at the far power level of Y-axis, 240. Different quality matrix can be used to define the best far focus, such as the highest MTF at certain spatial frequency, largest MTF area, highest Strehl Ratio and others. For the sake of specificity, the best far focus is defined as the highest MTF at 50 lp/mm. In order for the best far focus position to coincide with the far focus position of the multifocal diffractive lens with spherical base surface, the power of the spherical base surface must coincide with the average far power of the multifocal power profile of the multifocal base surface. The corresponding far power of the spherical base surface is called equivalent spherical power and the corresponding spherical base surface is called spherical base surface of equivalent power. The equivalent spherical power coincides with the average far power of the multifocal base surface 210 and is referenced to by the same horizontal broken line drawn at far power level of Y-axis, 240.

The same description can be applied to the opposite refractive surface by considering multifocal opposite surface instead of multifocal base surface. The opposite multifocal surface manifests best far focus defined by some quality matrix. It is compared with the opposite spherical surface of the power with the far focus coinciding with the best far focus of the opposite multifocal surface. This opposite spherical surface is called equivalent (spherical) power to the opposite multifocal surface is the powers coincide. The corresponding opposite spherical refractive surface is then called opposite spherical refractive surface of equivalent power. The spherical lens with the surfaces of equivalent powers is called the spherical lens of equivalent power and visa versa, spherical lens of equivalent power incorporates spherical surfaces of equivalent powers.

Deviations of the multifocal base surface power profile of the present invention from the equivalent power base surface are shown on the FIG. 5 as a deviation 270 at the region of intermediate power and a deviation 280 at the region of power that is below the average or best far power 240 of the multifocal power profile of the multifocal base surface. A power profile for intermediate and far powers can take different shapes with the outcome to produce the enhanced depth of focus around far focus as compared with the depth of focus produced by the equivalent power spherical base surface.

The diffraction groove widths now must follow the variable sag of the multifocal base surface profile in order for the wavefront shifts between the grooves to produce constructive interference at (−1)-order of diffraction allocated to near focus as being a single focus location in order to maximize the image contrast at near. The method of diffraction groove widths calculation per present invention is provided below.

Figure 6:
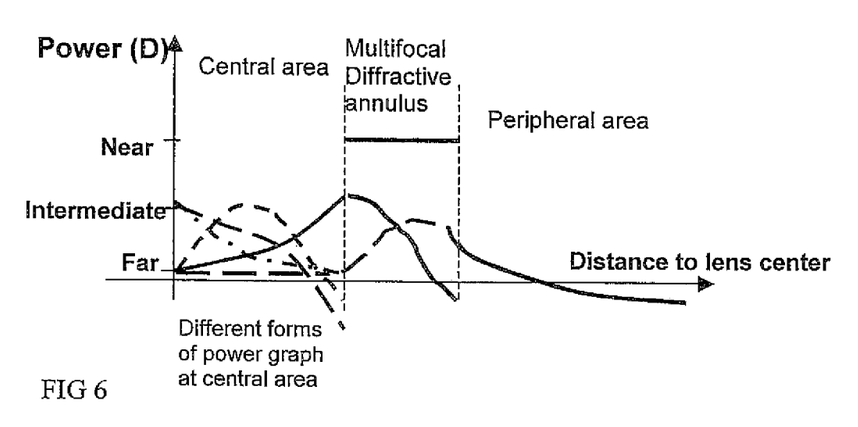
FIG. 6 shoes a Power Profiles of the lens described in the FIG. 4.

FIG. 6 is a Power graph of the lens described in the FIG. 4 where the power distribution along the central zone is represented by different variable power profiles.

Figure 7:
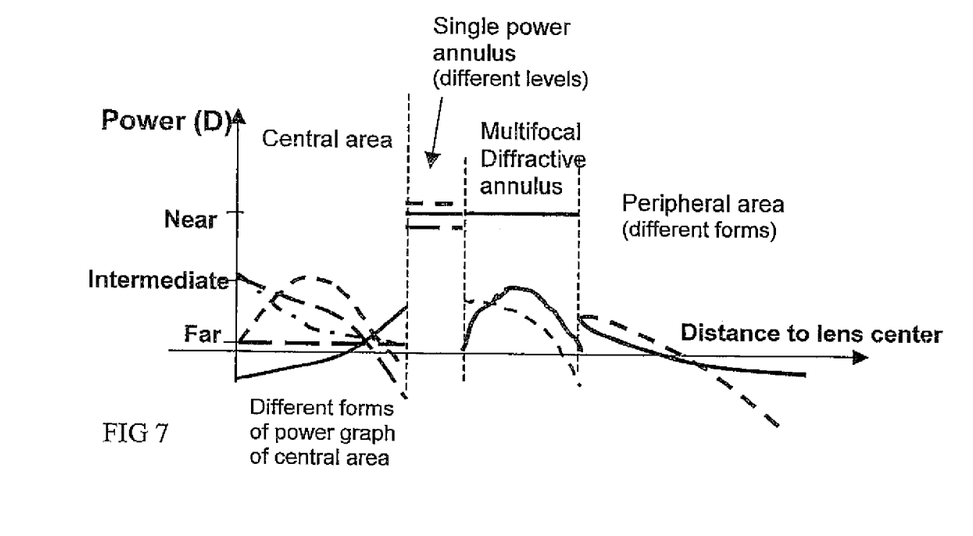
FIG. 7 shows Power Profiles of the lens described also on FIG. 4 but with different power profiles within the diffractive zone.

FIG. 7 is a Power graph of the lens described in the FIG. 4 where the power distribution along the central zone inside of the multifocal diffractive annulus is a combination of refractive zone of varying power profiles and single focus diffractive annulus (Kinoform) for near focus.

Figure 8A:
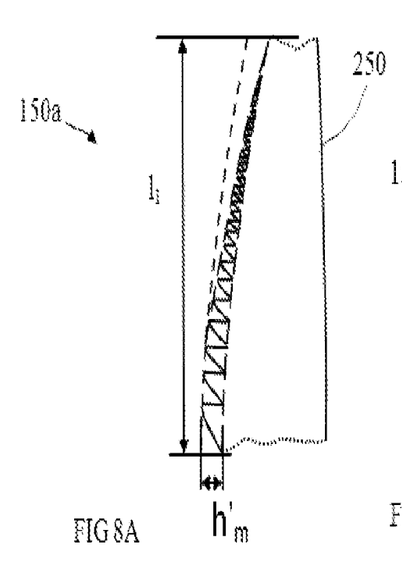
FIGS. 8A and 8B are side views of multifocal diffractive zone of the present invention.

FIG. 8A is a profile view of the multifocal diffractive portion of lens 150a of width $l_1$ and posterior surface 250. The width $l_1$ is about from 0.4 mm to 2.5 mm. The figure demonstrates groove height $h'_m$ that is continually reduced but in general they may be have the height reduction in steps. "Geometrical model" of the diffractive optic explains the reduction in grove height in order to direct the blaze ray in between the diffraction orders associated with far-intermediate zero-order and near foci non-zero order to split the light between aspheric multifocal 0-order and single focus (−1)-order though a rigorous diffraction theory is required to provide a fully quantitative solution for the groove widths, profile and heights meeting the specific transmittance requirements for far, intermediate and near foci.

Figure 8B:
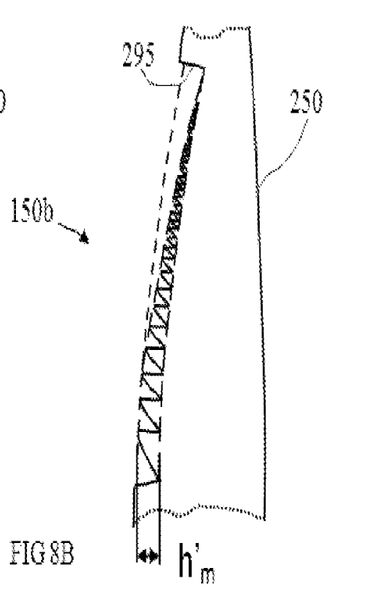

FIG. 8B is a profile view of multifocal diffractive zone of lens 150b similar to those described by FIG. 8A with both zones being recessed by the depth 295, which is at least as deep as the groove height ($h'_m$). This construction is particularly useful when involve soft material when the diffractive surface can be pressed against an ocular tissue and deform its shape. For instance, for placement at the posterior surface of the intraocular lens or contact lens that may interface with the ocular tissue and deform the groove shapes.

Figure 9:
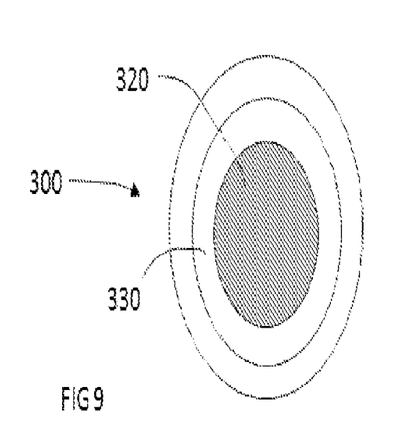
FIG. 9 is a plane view of a preferred embodiment of a lens made in accordance with the present invention, which has multifocal diffractive central zone and multifocal refractive zone outside of it that includes intermediate and far foci. The multifocal refractive zone may incorporate an enhancing DOF power profile form. The multifocal refractive zone or diffractive zone may be on the same or opposite lens surfaces.

FIG. 9 is a plan view of a preferred embodiment of the ophthalmic lens 300 made in accordance with the present invention which has multifocal diffractive central zone 320 FIG. 9 demonstrates the central zone 320 of a spherical configuration but other suitable configuration may be also utilized. For example, a multifocal diffractive zone 320 may also be a segment or annulus of variable radii. The refractive aspheric zone 330 is placed outside of the multifocal diffractive zone either on the same or opposite lens surface. The aspheric zone is to reduce aberrations of the lens at large pupils.

Figure 10:
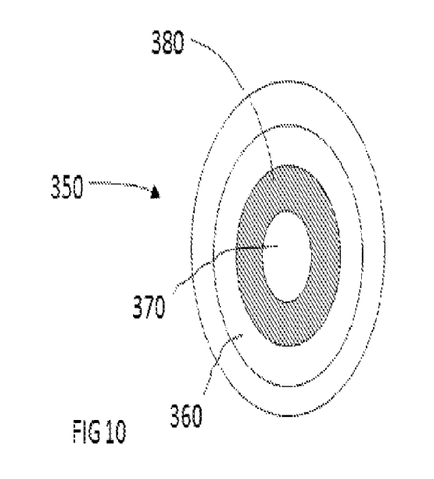
FIG. 10 is a plan view of preferred embodiment of a lens made in accordance with the present invention, which has multifocal diffractive zone as annulus and multifocal refractive zone outside of it with intermediate and far foci. The multifocal refractive zone may incorporate the enhancing DOF power profile form. The multifocal refractive zone or diffractive zone may be on the same or opposite lens surfaces.

FIG. 10 is a plane view of another preferred embodiment of an ophthalmic lens 350 made in accordance with the present invention which has multifocal diffractive zone 380 placed outside of the central refractive or diffractive zone 370 of a single power. A refractive aspheric zone 360 is placed outside of the multifocal diffractive zone either on the same or opposite lens surface. The aspheric zone is to reduce aberrations from the peripheral region of the lens at large pupils.

Figure 11:
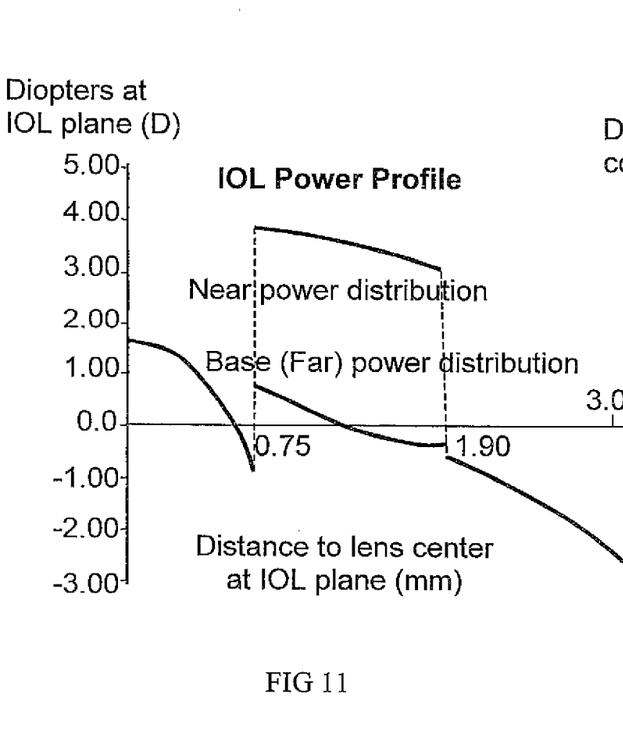
FIG. 11 is the example of an IOL Power Profile. The Power Profile includes the near power distribution and base surface power distribution. The base surface manifests a multifocal power profile with intermediate and far powers.

FIG. 11 is the example of an IOL Power Profile. The Power Profile includes the near power distribution and Base (Far) power distribution. The Zero axis is taken at the power of best distant focus defined as the best image quality in terms of modulation transfer function. The vertical axis is scaled in IOL diopters or so called reduced diopters defined at the IOL plane.

The lens of the particular example was made of PMMA with spherical anterior surface of radius 12.3 mm, 0.8 mm thickness and aspheric multifocal posterior surface. The latter consists of three aspheric zones: (1) refractive aspheric central zone of 1.5 mm diameter, (2) diffractive aspheric annular zone with 3.8 mm peripheral diameter and (3) refractive aspheric zone of 6 mm peripheral diameter.

Each zone is described by standard aspheric format:

$$z(r) = \frac{cr^2}{1 + \sqrt{(1 - c^2 r^2)}} + A_4 r^4 + A_6 r^6 + A_8 r^8 + A_{10} r^{10}$$

Where z(r)=surface sag; r=distance to the lens center; c=1/R=surface vertex curvature (R=surface vertex radius); $A_i$=aspheric coefficients.

TABLE 1

| Base Surface Zone parameters | | | |
|---|---|---|---|
| Parameters | Zone 1 | Zone 2 | Zone 3 |
| R (mm) | −20.80 | −22.00 | −26.65 |
| $A_i$ | $A_4$ = 0.0066461 | $A_4$ = 0.0015878<br>−0.000160836 | $A_4$ = 0.0001176<br>$A_6$ = 0.00003538346<br>$A_8$ = −0.0000009912011 |

The diffractive structure is placed within the second zone to produce near power in addition to distant and intermediate powers of the base surface. The near power distribution is elevated over the base power by Add Power and spread out within 3.1 D and 3.7 D range. The groove width of the diffractive structure is about 0.17 mm at the internal zone diameter to about 0.08 mm at the periphery. The groove radii square do not follow the linear function of formula 1. The phase coefficients per the formula 3 of the diffractive structure measured in radians are:

$$a_1=0.191405; a_2=18.525067; a_4=1.783861 \text{ and } a_6=-0.290676$$

Figure 12:
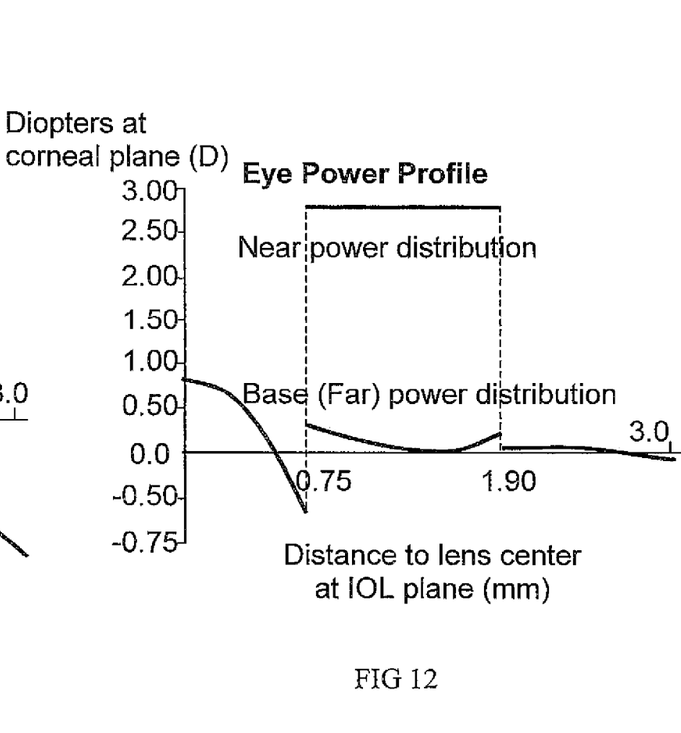
FIG. 12 is the example of an Eye Power Profile where the IOL is part of the Eye optical system. The Power Profile includes the near power distribution as a single power and base surface power distribution. The base surface manifests a multifocal power profile with intermediate and far powers.

FIG. 12 is the example of an Eye Power Profile where the IOL is part of the Eye optical system. The IOL is the same as one described on the FIG. 11. The Zero axis is taken at the power of best distant focus defined as the best image quality in terms of modulation transfer function. The vertical axis is scaled in diopters at corneal plane. The reciprocal of the corresponding dioptric power defines a distance to the viewing object in meters. The eye system is taken with typical corneal surfaces: Anterior surface of 7.8 mm of vertex radius and conic constant of −0.21 and posterior surface of 6.5 mm radius and conic constant of −0.23.

The remarkable outcome of the Power Profile with the described above IOL was that the Near Power was presented by a single power of 2.78 D for near viewing, i.e. the near object at around 0.36 m~14" from the eye is in focus. A single level of near power profile points out that the diffractive structure creates a spherical wavefront to channel all designated by the structure light to Near Focus thus maximizing the near focus efficiency. The explanation is that the interaction of the diffractive structure with the wavefront of the total optical system is such that it creates a spherical wavefront for near focus. As far as distant focus is concern, the multifocal structure of the base surface results in intermediate focus and broad depth of focus at distant focus.

Figure 13:
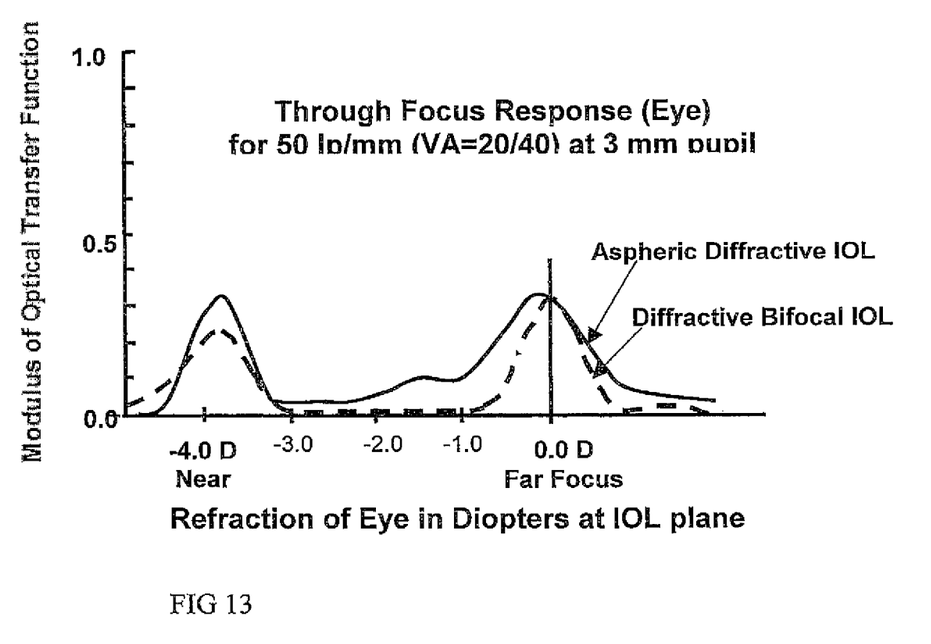
FIG. 13 demonstrates a Modulus of the Optical Transfer Function for different focus positions, so called Through Focus Response (TFR). The TFR graph represents image quality of the eye with preferred embodiment of the multifocal diffractive lens of the present invention.

FIG. 13 demonstrates a Modulus of the Optical Transfer Function for different focus positions, so called Through Focus Response (TFR). The TFR graph represents image quality of the eye with preferred embodiment of the aspherical diffractive multifocal lens per FIG. 12 and transmittance function of its apodized diffractive bifocal zone per Table 2 below.

The diffractive structure of the annular zone of radii between 0.75 mm and 1.0 mm is for near vision as 100% of light is transmitted to near focus. The diffractive bifocal zone occupies the width between 1.0 and 1.9 mm radii. The design includes the groove apodization defined by the transmittance to Far and Near foci:

$$T=T_0 \cdot (1-T_1 \cdot r - T_2 \cdot r^2 - T_3 \cdot r^3 - T_4 \cdot r^4).$$

TABLE 2

| | Transmittance | | | | |
|---|---|---|---|---|---|
| Efficiency | $T_0$ | $T_1$ | $T_2$ | $T_3$ | $T_4$ |
| Far focus | 2.508375 | 3.010962 | −2.98324 | 1.074313 | −0.13188 |
| Near focus | −16.4189 | 3.593128 | −4.31017 | 2.167969 | −0.3942 |

Thus, the apodization of the grooves within the diffractive bifocal zone is such that it starts with the height to direct all light along the diffraction order associated with near focus and then the heights are reduced to create the transmittance described by Table 2 until reaching close to zero to direct all light along the diffraction order associated with far focus.

The TFR of the preferred aspherical multifocal diffractive lens is compared with TFR of the multifocal diffractive lens where light is equally split between far and near foci (40.5% at each focus for the design wavelength with the rest of light is distributed between higher diffraction orders) for 3 mm lens aperture. The graphs demonstrate the remarkable advantage of the preferable aspherical multifocal diffractive lens over the multifocal diffractive lens by manifesting Intermediate vision capability in addition to the improved Near and Far vision capabilities as well as broad Depth of Focus to reduce sensitivity to a small refractive error.

Figure 14:
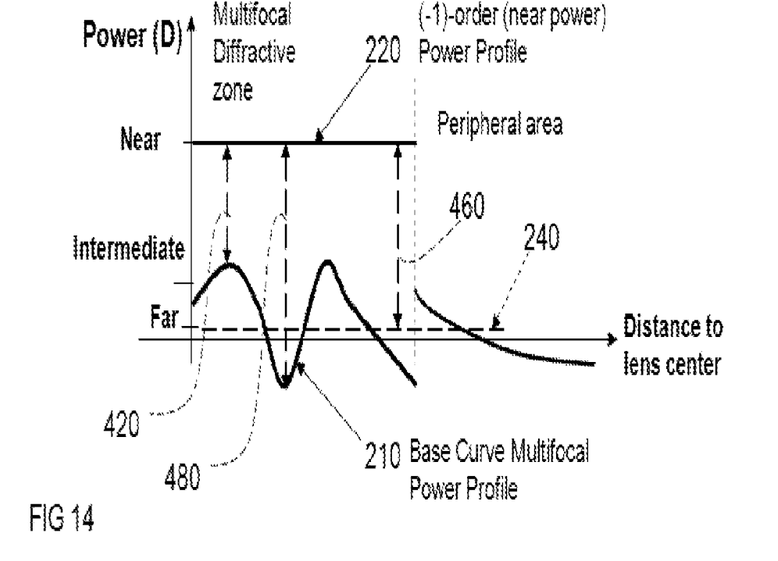
FIG. 14 demonstrates the power profile of the multifocal lens of the present invention referenced to in the FIG. 5. It introduces a concept of variable add power according to the power variation of the multifocal base surface. This is also applicable to the multifocal opposite surface instead.

FIG. 14 returns to the power profiles of the multifocal lens in accordance with the present invention introduced in the FIG. 5. It demonstrates the near power as the horizontal line of constant power 220 formed by the constructive interference at (−1)-order of diffraction to maximize near image contrast. A separation between near power 220 and the average or best power 240 of multifocal power profile of the multifocal base surface is called average add power 460. The average power of the multifocal base surface coincides with the equivalent power spherical base surface so the average add power equals the add power of the corresponding multifocal diffraction lens of the prior art with spherical base surface of equivalent power or aspheric base surface of equivalent power that corrects for spherical aberration of the spherical base surface of equivalent power.

A local add power is defined as a separation between the near power and each local point of the power profile produced by the power variation of a multifocal base surface or multifocal opposite refractive surface. A local add power can be below the average add power or above the average add power. For instance, separation between near power 220 and intermediate power of the multifocal base curve is called a local low add power 420 because it manifests a reduced magnitude from the average add power 460. A separation between near power and power of the multifocal base curve that is above the average power of the multifocal base curve is called a local high add power 480 because it manifests an increased magnitude from the average add power 460. The presence of the multifocal base surface or multifocal opposite refractive surface of the present invention results in a variable local add power across the multifocal diffractive lens whereas the add power of a multifocal diffractive lens of the prior art is always a constant value.

Figure 15:
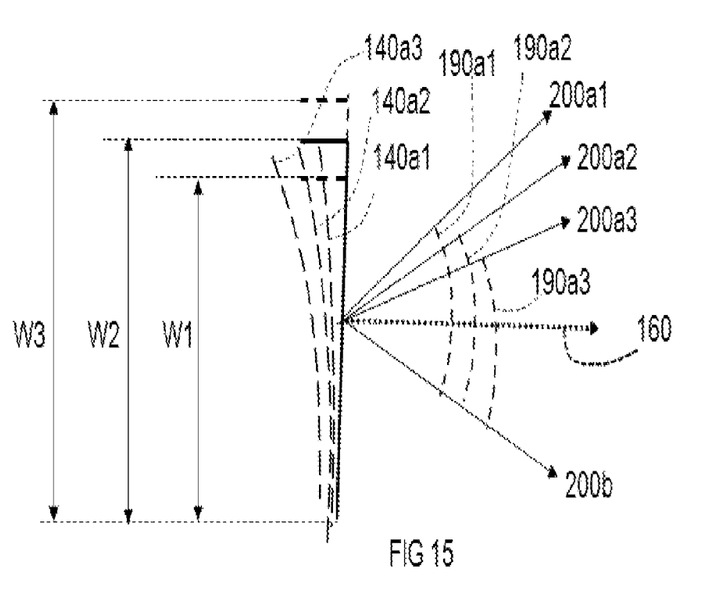
FIG. 15 demonstrates how variable add power effects the diffraction groove widths of the multifocal diffractive lens of the present invention versus the diffraction groove widths of a multifocal diffractive lens of a prior art where the add power is of a constant value.

FIG. 15 demonstrates an impact of varying directions of zero-order diffraction on the groove widths required to produce constant near focus, for instance, as (−1)-order diffraction.

In terms of diffraction optic, the direction of zero-order diffraction varies in accordance with the present invention. The range of zero-order diffraction rays is introduced at a single location of i-groove at the distant $r_i$ from the lens center in order to demonstrate a how the variation in local add power impacts the corresponding groove width. For instance, the multifocal base surface shape 140$a2$ is responsible for the ray 200$a2$ directed to the focus position that corresponds to the average power (best focus position) 240 of the multifocal diffractive lens in accordance with the present invention. The multifocal base surface shape 140$a1$ is responsible for the ray 200$a1$ directed to the focus which is further away from the average focus position, i.e. the corresponding power is below the average power, for instance shown as the deviation 280 from the average power on FIG. 5. The multifocal base surface shape 140$a3$ is responsible for the ray 200$a3$ directed to an intermediate focus position, for instance shown by the deviation 270 from the average power on FIG. 5.

Changes in the direction of zero-order diffraction effect a phase shift in (−1)-order diffraction and the groove widths must be adjusted accordingly to maintain phase function cycles by 2π period between the groove boundaries in order to maintain constructive interference at (−1)-order diffraction to produce a constant near focus. The process of the groove widths adjustment is illustrated on the FIG. 15 by utilizing the term angular add power. The angular add power between the rays 200a2 and 200b is 190a2 and equals the angular add power of the multifocal diffractive lens with spherical base surface of equivalent power. The corresponding i-groove width produces $2\pi$ phase shift along the ray 200b resulting in the constructive interference at the near focus and is designated as "W2" on the FIG. 15. This is equivalent the groove width at $r_i$ distance from the multifocal diffractive lens center of the prior art with equivalent power spherical base surface as calculated per formula (1).

The angular add power between the rays 200a1 and 200b is 190a1 which produces local high add power. The angle between zero- and (−1)-orders of diffraction has increased and, therefore, the phase shift between the groove's boundaries in the direction of ray 200b would pass beyond $2\pi$ phase shift. A constructive interference can't occur at (−1)-order of diffraction corresponding to near focus if the same groove width W2 is maintained at the corresponding region of multifocal base surface thus degrading the near image. The corresponding groove width at the corresponding region of multifocal base surface must be reduced to compensate for the phase shift excess beyond $2\pi$ phase shift between groove's boundaries in the direction of the ray 200b. The corresponding groove width is designated as "W1" on the FIG. 15. As a result of this groove width compensation, the constructive interference is restored at the constant near focus position corresponding to the near power level 220.

The angular add power between the rays 200a3 and 200b is 190a3 which produces local low add power. The angle between zero- and (−1)-orders of diffraction has reduced and, therefore, the phase shift between the groove's boundaries in the direction of ray 200b does not reach $2\pi$ phase shift. A constructive interference can't occur at (−1)-order of diffraction corresponding to the designated near focus for the groove width W2 if used at the corresponding region of the multifocal base surface thus degrading the near image. The groove width must be increased at the corresponding region of the multifocal base surface to compensate for the phase shift shortage to $2\pi$ phase shift between groove's boundaries in the direction of the ray 200b. The corresponding groove width is designated as "W3" on the FIG. 15. As a result of this groove width compensation, a constructive interference is again restored at the constant near focus position corresponding to the near power level 220.

The prior art method of determining groove widths per formula (1) produces a near image degradation if applied to the multifocal diffractive lens of the present invention which includes a multifocal base surface or multifocal opposite refractive surface. A new method of groove width calculation must replace formula (1) used in the prior art due to the presence of the multifocal base surface or multifocal opposite refractive surface in accordance with the present invention.

A new method of producing diffractive multifocal surface in accordance with the present invention has been discovered. It includes:

a) selecting the location (central or annular) and surface placement (opposite or base surface) for the multifocal surface;

b) selecting a multifocal form that enhances DOF around far (distant) focus or surface variation at intermediate and far foci;

c) selecting a location (central or annular) and surface placement (front or back) for the diffractive multifocal structure.

d) calculating diffractive structure phase coefficients that produce near spherical wavefront for near focus for a selected add power to serve as non-zero order diffraction for the aspheric diffractive lens with multifocal zero-order diffraction. Usually (−1)-order diffraction is allocated to near focus.

$$\Phi_{-1}(r) = \frac{2\pi}{\lambda}[a_1 r + a_2 r^2 + \ldots + a_n r^n] \qquad (3)$$

Formula (3) is (−1)-order (near focus) phase function with phase coefficients $a_i$ calculated over the contribution of the eye optical system that includes the multifocal opposite or base surface in a form of their sags contribution. The resulted wavefront should be close to spherical wavefront to maximize the efficiency for near image. The corresponding optimization for the phase coefficients $a_i$ can be performed by conventional optical design software, Zemax, for instance;

e) numerically calculating the first groove shape that produces the defined above phase coefficients that directs 100% of light to the diffractive near focus. The groove width is defined by the phase function modulo $2\pi$, i.e. phase function cycles by $2\pi$ period where the groove height drops to zero for each consecutive groove, formula (4).

$$h(r_i) = \{[\Phi_{-1}(r_i)]_{2\pi}\} \frac{\lambda}{2\pi(n - n')}, \qquad (4)$$

where $r_i$=radial numerical sampling with small enough step, for instance, 5 microns step The maximum groove height is defined by formula 2, i.e.

$$\frac{\lambda}{(n - n')}$$

for (−1)-order diffraction.

Phase function could be of modulo $2\pi p$ where p=2, 3, etc. for multi-order diffraction design.

The groove's width is not defined now by a simple formula (1) where the base wavefront is close to spherical shape to produce single focus zero-order diffraction for distant focus. The width becomes derivative of the complex wavefront shape produced by the eye optical system that includes a multifocal opposite surface or multifocal base surface.

A new method of producing the light distribution between zero-order and (−1)-order diffraction is also discovered. The method that is based on the "geometrical model", i.e. defined by the direction of the blaze ray and the boundary conditions of the diffraction efficiencies as defined by the rigorous diffraction theory:

(1) equal diffraction efficiencies of 40.5% for zero-order and (−1)-order diffractions if the blaze ray direction is exactly in the middle between the directions of these orders;

(2) diffraction efficiency for distant or near is 100% if the blaze ray direction coincides with a direction of either zero-order or (−1)-order diffraction.

FIG. 2 provided a graphical explanation of the geometrical model. In accordance with this model a relative direction of the blaze ray can be translated to blaze height by the formula 5:

$$h'(r_i) = \frac{S - [T_0(r_i) - T_{-1}(r_i)]}{2S} \cdot h(r_i) = K(r_i) \cdot h(r_i) \quad (5)$$

where
- $h(r_i)$ is calculated in accordance to formula 4;
- $T_0(r_i)$=transmittance to or diffraction efficiency of 0-order diffraction;
- $T_{-1}(r_i)$=transmittance to or diffraction efficiency of near focus, i.e. (−1)-order diffraction;
- $T_0(r)+T_{-1}(r)$=S, where S is within 0.81 to 1.0.
- Coefficient $K(r_i)$ acts as the normalization coefficient for transmittance to otherwise the diffractive structure with 100% transmittance to (−1)-order for near focus.

Parameter "S" of the formula (5) is 0.81 if the blaze ray direction is exactly in the middle between the directions to near and distant foci and, as a result, equal efficiencies for near and distant foci of 40.5%. It is 1.0 if blaze ray direction coincides either with zero-order diffraction or (−1)-order diffraction and, as a result, the corresponding diffraction efficiency for distant or near is 100%. One can take S as a constant between 0.81 and 1.0, say 0.9 if the blaze ray angle varies between directions to near and distant foci. More sophisticated option is to vary "S" within 0.81 and 1.0 depending upon the actual direction of the blaze ray for a given groove's location $r_i$ in reference to the direction to distant and near foci. It could take different form and linear one is represented by the formula below:

$$S = 0.19 \cdot X + 0.81, \text{ where } X = \left[\frac{T_0(r_i) - T_{-1}(r_i)}{T_0(r_i) + T_{-1}(r_i)}\right]^2.$$

The process of diffraction structure calculation continues:
f) selecting the step height for the first groove of the diffractive zone to create a required balance of light between multifocal zero-order diffraction and (−1)-order diffraction for near focus. Different methods of groove height calculation can be used and method based upon the "geometrical model" was described above.
g) the process of steps (e) and (f) calculations is repeated for the consecutive grooves until reaching the peripheral edge of the multifocal diffractive zone.

What is claimed is:

1. A multifocal diffractive ophthalmic lens comprising:
a lens element having an anterior and a posterior surface;
a diffractive multifocal zone disposed on one of the anterior and posterior surfaces, said diffractive multifocal zone including structure producing near focus;
an opposite refractive zone disposed on another of the anterior and posterior surfaces, incident light passing consecutively through both zones;
a multifocal base surface of said diffractive multifocal zone or opposite refractive zone shaped to produce far and intermediate foci by the multifocal diffractive ophthalmic lens, where diffractive groove widths having the multifocal base surface are adjusted from a width defined by a formula $$f_m = \frac{r_j^2}{jm\lambda}$$

to produce close to phase function cycles by $2\pi$ period between a diffractive groove boundary, where "$\lambda$" is a design wavelength "$f_m$" is a focal length "j" is a groove order, "$r_j$" is a radial boundary position of j-order groove, and "m" is an m-order diffraction.

2. The lens according to claim 1 wherein the refractive and diffractive multifocal zones are annuli.

3. The lens according to claim 1 wherein the refractive and diffractive multifocal zones are central zones.

4. The lens according to claim 1 wherein the diffractive multifocal zone comprises a plurality of grooves, the grooves being anodized towards lens periphery from a height directing a larger percentage of light along a diffractive order associated with near focus to a height directing the larger percentage of light along a diffractive order associated with distant focus.

5. The lens according to claim 1 wherein the diffractive multifocal zone is recessed into one of the anterior and posterior surfaces.

6. A multifocal diffractive ophthalmic lens comprising:
a lens element having an anterior and a posterior surface;
a diffractive multifocal zone disposed on one of the anterior and posterior surfaces, said diffractive multifocal zone including groove structure producing focal length $f_m$ of m-order diffraction for near focus;
an opposite refractive zone disposed on another of the anterior and posterior surfaces, incident light passing consecutively through both zones;
an intermediate focus producing part of said diffractive multifocal lens where the part is either at a base surface of said diffractive multifocal zone or opposite refractive zone, wherein the intermediate focus producing part is shaped to produce an intermediate focus of at least 0.5 D from far focus of said multifocal diffractive ophthalmic lens; and
wherein a width of a diffractive groove of order "j" of said diffractive multifocal zone is increased at the intermediate focus producing part of said multifocal diffractive ophthalmic lens from a width of a groove of order "j" defined by a radial boundary position $r_j$ that results in a same focal length magnitude per a formula $$f_m = \frac{r_j^2}{jm\lambda}$$

for said near focus in order to produce phase function cycles by $2\pi$ period between boundaries of said increased width of the diffractive groove of order "j", where "$\lambda$" is a design wavelength and "m" is an m-order diffraction.

* * * * *